United States Patent [19]

Pace et al.

[11] Patent Number: 4,674,332
[45] Date of Patent: Jun. 23, 1987

[54] LASER INDUCED ACOUSTIC GENERATION FOR SONIC MODULUS

[75] Inventors: Sal A. Pace, Trenton, N.J.; Simon S. Salama, Newton, Pa.

[73] Assignee: Union Camp Corporation, Wayne, N.J.

[21] Appl. No.: 831,485

[22] Filed: Feb. 20, 1986

[51] Int. Cl.$^4$ .............................................. G01N 29/04
[52] U.S. Cl. ........................................ 73/597; 73/643
[58] Field of Search ........................ 73/597, 643, 159

[56] References Cited

U.S. PATENT DOCUMENTS

| 4,137,991 | 2/1979 | Melcher et al. | 73/643 |
| 4,291,577 | 9/1981 | Baum et al. | 73/597 |
| 4,338,822 | 7/1982 | Yamaguchi et al. | 73/643 |
| 4,353,256 | 10/1982 | Moorey | 73/597 |
| 4,446,735 | 5/1984 | Weilacher | 73/597 |
| 4,567,769 | 2/1986 | Barkhouparian | 73/643 |

Primary Examiner—Anthony V. Ciarlante
Attorney, Agent, or Firm—Kane, Dalsimer, Kane, Sullivan and Kurucz

[57] ABSTRACT

A method and device which measures the velocity of ultrasonic waves in a moving web is disclosed. The excitation source is a laser or other device which produces short intense light pulses and the detection system is either a piezoelectric transducer or a microphone. The latter obviates any need for physical contact with the web in order to carry out tests for strength parameters as the web is manufactured.

3 Claims, 1 Drawing Figure

LASER INDUCED ACOUSTIC GENERATION FOR SONIC MODULUS

BACKGROUND OF THE INVENTION

1. Field of the Invention

This invention relates to a method and apparatus for the nondestructive measurement of physical properties of a web or sheet, for example a sheet of paper.

2. Brief Description of the Prior Art

Paper manufactured for various applications and needs, must meet certain strength requirements. Such strength parameters are usually determined by tests which in the process destroys the sample being tested, for example, by the application of stress until the paper tears. This kind of destructive testing is obviously undesirable in some circumstances. For example, these tests may be performed on paper that has been wound on a reel. It must be cut from the reel and is usually conditioned to a standard moisture prior to being tested. This process requires a considerable time, which is undesirable for a test method used to control a paper machine since considerable off-quality product can be produced prior to detection and correction.

U.S. Pat. No. 4,291,577 described a method and apparatus for the nondestructive testing of paper as it is produced in a continuous fast moving web. The invention utilizes the known fact that many of the strength parameters of paper are related to Young's modulus of elasticity and the shear modulus. The moduli can be correlated with the velocity of sound waves traveling through the paper web. A transmitting transducer sends a mechanical signal to the paper and a receiving transducer picks up the ultrasound signal from the paper. By knowing the time it takes the ultrasonic waves to travel through the paper and the distance they travel the velocity of the ultrasonic waves can be calculated. The transducers are located in wheels which are in physical contact with the moving paper web. While the testing may be carried on in a nondestructive way while the paper is being produced, such a device is inherently complex. Thus, the wheels containing the sending and receiving transducers must be exactly synchronized. The sending transducer must contact the sheet and produce an acoustic wave which must be detected 1 to 100 microseconds later at some receiving transducer a short distance away. The receiving transducer must remain in contact with the sheet long enough so that it will not miss the first oscillation of the acoustic pulse which has been generated. These are serious impediments to the test method.

More importantly, the signal strength depends on the force with which mechanical sending and receiving transducers are applied to the moving web. This factor alone is a serious impediment to the use of the method, creating stress forces on both the apparatus and the moving web.

In addition, the physical properties of the paper web depend to a large extent on the elastic and shear moduli in the thickness or out-of-plane direction which present on-machine devices cannot measure.

Obviously it would be desirable to develop a method and apparatus which would test paper nondestructively, both in the in-plane and out-of-plane direction in the absence of physical contact or with minimal force applied to the web. The present invention answers the need for such apparatus by utilizing a laser beam for exciting the necessary acoustic signal in the web, thus eliminating one point of physical contact. The receiver can either be a mechanical transducer in contact with the paper or a microphone not in physical contact with the paper, thus minimizing, or in the case of a microphone, eliminating points of physical contact and stress.

The use of laser beams to generate acoustic waves is described in U.S. Pat. No. 4,169,662.

SUMMARY OF THE INVENTION

The invention comprises a method and a device for nondestructively testing a physical property of a workpiece such as a moving sheet or web of paper. In one embodiment, a beam of laser light or other short light pulse producing device is used for excitation of an acoustic wave at a point on a first planar surface of the sheet or web and a piezoelectronic transducer in a wheel configuration is used at a point on a second planar surface of the sheet or web as the means of detecting the velocities of the ultrasound waves passing from the first surface to the second surface, traversing the thickness of the sheet or web.

BRIEF DESCRIPTION OF THE DRAWINGS

The FIGURE is a schematic view of a device used in the method of the invention to detect out-of-plane acoustic waves generated by laser light.

DETAILED DESCRIPTION OF THE INVENTION

Figure 1:
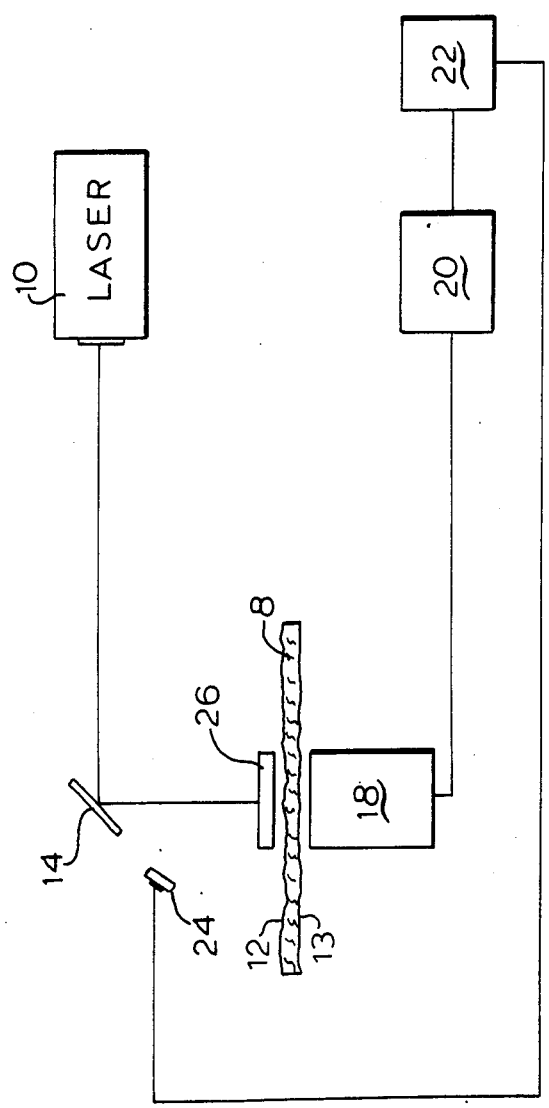

The method of the invention may be used to measure strength characteristics of a wide variety of light absorbing test materials including, but not limited to, sheets or webs of paper, synthetic polymeric resins and the like.

According to one embodiment of the method of the present invention, a paper web as it is being manufactured on a papermaking machine is subjected to short pulses of light, preferably laser radiation, for the purpose of determining mechanical strength properties of the paper. One possible theory of the present invention is that the molecules in the paper which absorb the incident photons, re-emit the energy through several channels, the most efficient of which is by a localized heat pulse in the paper. Heat thus produced in turn generates mechanical stress in the structure of the paper which manifests itself as an acoustic wave. The acoustic wave propagates from the illuminated point outward through the paper. The acoustic pulse generated on, for example an upper surface of the paper sheet or web, may be detected at the lower surface of the sheet, away from the point of generation, to obtain a measurement of the acoustic velocity in the body of the sheet.

The initial degree of excitation achieved with the light source depends on the wavelength use. Convenient wavelengths lie in the range from about 200 to about 10,000 nm. Use of optimal wavelengths within this range results in a greater absorption of the incident energy, and therefore for a stronger acoustical signal. Any known sub-microsecond pulsed light source producing the desired effect may be used, preferably a laser source. The measurements of longitudinal and shear wave velocities propagated through the body of the paper web can then be related to the Young's moduli, shear moduli, and Poisson's ratios for paper. This type of on-line determination can be used in a closed-loop control system to adjust and optimize paper machine variables, such as rush-drag ratio, level of refining, wet pressing, etc. during manufacture of the paper web.

The measurement of the velocity of the acoustic waveform may also be used to obtain information regarding the interaction of the waveform with the paper sheet through which it traveled such as, the density of the paper, as well as the orientation of various microscopic elements in the paper such as cellulosic fibers.

In one embodiment of this invention, the excitation of the acoustic waveform is carried out with a beam of laser light and detection of the sonic waves is achieved with a bimorph piezoelectric transducer which makes brief physical contact with the web of paper on a side opposite to the surface of the sheet receiving the laser light excitation. In this embodiment both longitudinal and shear waves can be discerned by orienting the piezoelectric transducer motion parallel to the direction of motion of the sound wave or perpendicular to the direction of motion of the sound wave, respectively. This embodiment is schematically illustrated in the accompanying drawing. A source of laser light of 337.1 nm wavelength from a Nitrogen ($N_2$) laser 10 is directed on the absorbing upper surface 12 of paper sheet 8 by reflection from a mirror 14 focused onto a window 26 which applies a pressure of known value onto the paper to maintain a constant thickness. The source of light 10 might also be any other device which produces short intense light pulses on the order of one microsecond or less such as a flash lamp. The detection probe, which is in this case a piezoelectric transducer 18, is placed in contact with the lower surface 13 of the paper sheet 8 at a fixed and predetermined point opposite the point of impingement of the laser beam. In the embodiment shown in the FIGURE, the detection system consists of the piezoelectric transducer 18, a preamplifier 20, a transient digitizer 22 and a photodiode 24.

As shown in the FIGURE, the acoustic signal picked up by the transducer 18 is converted to an electrical signal, and transmitted to the amplifier 20. The amplified signal is then transmitted to the transient digitizer 22. The transient digitizer 22 measures the time between the firing of the laser as detected by the photodiode 24 and the reception of the electrical signal by the transducer 18. The time measured includes electrical transmission time in electrical cables, etc., but this added time may be calculated and subtracted to obtain the transmission time of the acoustic wave through the thickness of the body of the paper sheet 8. The measured transmission time of the longitudinal acoustic wave may be averaged. The ratio of thickness to time of flight of the acoustic wave is the velocity of the acoustic wave through the paper thickness. The piezoelectric transducer 18 can detect a longitudinal acoustic wave or shear acoustic wave depending on the orientation of the crystal used in the manufacture of such a piezoelectric transducer. The velocities may be used to calculate Young's modulus of elasticity while the transmission time for the shear acoustic wave can be used to calculate the shear modulus and both used to determine the strength properties of the Paper sheet 8.

The following examples describe the manner and the process of making and using the invention and set forth the best mode contemplated by the inventors for carrying out the invention.

Where the measurements of acoustic signals are given, the acoustic signals produced by laser excitation of the paper substrate were analyzed with a piezoelectric system as shown in the drawing of the FIGURE.

The excitation source was a Molectron $N_2$ laser which produces a fundamental emission wavelength of 337.1 nm with a pulse duration of 10 nanoseconds. The light pulse is directed onto one planar surface of a sheet of paper to populate different acoustic modes in the paper. The acoustic waves are then detected on the opposite side of the sheet of paper as the excitation pulse traverses the thickness of the paper sheet. Determination of the out-of-plane wave velocities, as described above, serves to determine the physical properties of the paper sheet without destruction of the sheet.

EXAMPLE 1

In this example a comparison is made between longitudinal wave velocities in the out-of-plane direction (using apparatus of FIG. 1) between the laser induced generation and the piezoelectric transducer generation for four types of paper grades. The data indicate good agreement between the two types of measurement for the out-of-plane longitudinal velocities.

| Sample No. | Sample Type | Longitudinal Wave Velocity (Km/sec) | |
| --- | --- | --- | --- |
| | | Laser | Piezoelectric Transducer |
| 1 | Commercial Linerboard (42#/MSF) | 0.27 | 0.31 |
| 2 | Commercial 50# Multiwall | 0.47 | 0.52 |
| 3 | Commercial White Forms Bond | 0.33 | 0.38 |
| 4 | Commercial Blotter Paper | 0.38 | 0.36 |

EXAMPLE 2

In this example we demonstrate the capability of the laser induced system to generate and detect shear waves in the out-of-plane mode, in one commercial sample of paper. The laser induced data agrees well with the piezoelectric contacting transducer results.

| Sample No. | Sample Type | Longitudinal Wave Velocity (Km/sec) | |
| --- | --- | --- | --- |
| | | Laser | Piezoelectric Transducer |
| 1 | Commercial Linerboard (42#/MSF) | 0.40 | 0.44 |

What is claimed is:

1. A method of non-destructively testing a physical property of a light absorbing, moving continous sheet of paper, said sheet having an upper surface, a lower surface and a sheet body between upper and lower surfaces, which comprises;
   beaming a source of short light pulse and amplitudes at one of said upper and lower surfaces of said light absorbing workpiece; and
   measuring the velocity of the ultrasonic waves produced by the thermal effect induced by the light pulse and travelling through the sheet body to the other of said upper and lower surfaces of the workpiece sheet.

2. A method of non-destructively testing a physical property of a light absorbing, moving sheet of paper, said sheet having a first planar surface, an opposite, second planar surface, and a body of predetermined thickness between the first and second planar surfaces, which comprises;

beaming a source of short light pulses at the first planar surface of said light absorbing sheet;

whereby ultrasound waves responsive to the thermal effect induced by the light pulses traverse the body of the sheet; and detecting the waves at the second planar surface by means of a piezoelectric transducer.

3. In a method of non-destructively testing a physical property of a light absorbing, moving web of paper having a first planar surface and a second planar surface with an intervening web body the improvement whereby all physical contact with the web is eliminated, comprising;

beaming a source of short light pulses at the first planar surface of said light absorbing moving web; and detecting the ultrasound velocities responsive to the thermal effect induced by the light pulses at the second planar surface of the web.

* * * * *